United States Patent
Shao et al.

(10) Patent No.: US 11,696,937 B2
(45) Date of Patent: Jul. 11, 2023

(54) GLYCOPEPTIDE COMPOUNDS HAVING ACTIVITY OF RESISTING DRUG-RESISTANT BACTERIA, AND PREPARATION METHOD AND APPLICATION THEREOF

(71) Applicants: Shanghai LaiYi Center For Biopharmaceutical R&D Co, Shanghai (CN); Zhejiang Medicine Co., Ltd., Shaoxing (CN)

(72) Inventors: Chang Shao, Shanghai (CN); Mei Ge, Shanghai (CN); Lingao Ruan, Shanghai (CN); Wei Wei, Shanghai (CN); Xing Xia, Shanghai (CN); Min Rao, Shanghai (CN); Qingqian Meng, Shanghai (CN); Minyu Luo, Shanghai (CN)

(73) Assignees: Shanghai LaiYi Center For Biopharmaceutical R&D Co., Ltd., Zhejiang (CN); Zhejiang Medicine Co., Ltd., Zhejiang (CN)

( * ) Notice: Subject to any disclaimer, the term of this patent is extended or adjusted under 35 U.S.C. 154(b) by 0 days.

(21) Appl. No.: 16/978,688

(22) PCT Filed: Mar. 4, 2019

(86) PCT No.: PCT/CN2019/076826
§ 371 (c)(1),
(2) Date: Sep. 5, 2020

(87) PCT Pub. No.: WO2019/170046
PCT Pub. Date: Sep. 12, 2019

(65) Prior Publication Data
US 2021/0093691 A1    Apr. 1, 2021

(30) Foreign Application Priority Data
Mar. 6, 2018  (CN) .................. 201810183928.6

(51) Int. Cl.
*A61K 38/14* (2006.01)
*A61P 31/04* (2006.01)
*A61K 9/00* (2006.01)
*A61K 47/02* (2006.01)

(52) U.S. Cl.
CPC ............ *A61K 38/14* (2013.01); *A61K 9/0019* (2013.01); *A61K 47/02* (2013.01); *A61P 31/04* (2018.01)

(58) Field of Classification Search
CPC ...... A61K 38/14; A61K 9/0019; A61K 47/02; A61K 38/00; A61P 31/04; C07K 9/008; C07K 9/006; C07K 1/00
See application file for complete search history.

(56) References Cited

U.S. PATENT DOCUMENTS

| | | | |
|---|---|---|---|
| 5,840,684 A * | 11/1998 | Cooper | C07K 9/008 530/322 |
| 6,635,618 B2 * | 10/2003 | Leadbetter | A61K 9/4858 514/2.4 |
| 8,420,592 B2 * | 4/2013 | Lehoux | A61P 17/00 514/1.1 |

FOREIGN PATENT DOCUMENTS

| CN | 101928331 A | 12/2010 |
|---|---|---|
| CN | 108409837 A | 8/2018 |

OTHER PUBLICATIONS

Allen et al (The Journal of Antibiotics, Aug. 1997, vol. 50, No. 8, 677-684) (Year: 1997).*
Patani et al (Chem. Rev., 1996, 96, 3147-3176) (Year: 1996).*
(Continued)

*Primary Examiner* — Sudhakar Katakam
(74) *Attorney, Agent, or Firm* — Ashok Tankha

(57) ABSTRACT

The present invention discloses glycopeptide compounds having activity of resisting drug-resistant bacteria, conforming to glycopeptide compounds represented by general formula (I),

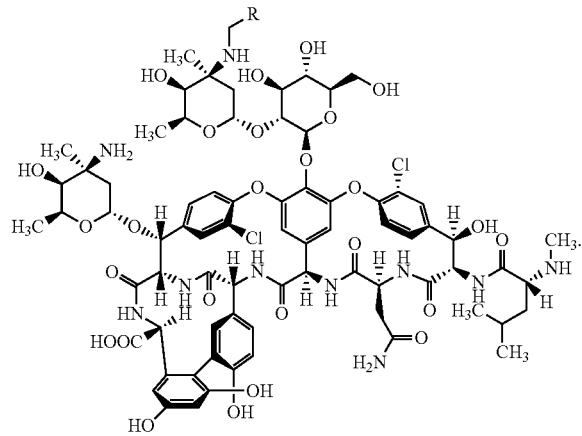

(I)

The present invention also provides a preparation method for and an application of the glycopeptide compounds. Upon testing, compared with a second-generation glycopeptide drug oritavancin, the glycopeptide antibiotic compounds have higher inhibition activity on drug-resistant bacterial strains, especially MRSA or VRE. Further testing shows that most of the glycopeptide compounds have safety higher than that of oritavancin and can be prepared into drugs for treating or preventing diseases caused by various bacterial infections, such as skin and soft tissue infections, meningitis, sepsis, pneumonia, arthritis, peritonitis, bronchitis, and empyema.

2 Claims, No Drawings

(56) References Cited

OTHER PUBLICATIONS

King et al (Med. Chem., Principle and Practice, 1994, 206-225) (Year: 1994).*
PTAB Doc (Appeal 2015-002393, 2015) (Year: 2015).*
Cooper_1998, U.S. Pat. No. 5,840,684 (Year: 1998).*

* cited by examiner

GLYCOPEPTIDE COMPOUNDS HAVING ACTIVITY OF RESISTING DRUG-RESISTANT BACTERIA, AND PREPARATION METHOD AND APPLICATION THEREOF

CROSS-REFERENCE TO RELATED APPLICATIONS

This is a national phase application of PCT application number PCT/CN2019/076826, filed in the State Intellectual Property Office of China on Mar. 4, 2019, titled "Glycopeptide Compounds Having Activity Of Resisting Drug-Resistant Bacteria, And Preparation Method And Application Thereof", which claims priority to and benefit of Chinese patent application No. 201810183928.6, filed on Mar. 6, 2018. The specifications of the above referenced patent applications are incorporated herein by reference in their entirety.

FIELD OF THE INVENTION

The present invention belongs to the technical field of medicinal chemical synthesis, and specifically relates to novel glycopeptide compounds being used for drugs of treating infectious diseases. The present invention also relates to the preparation method and application thereof.

BACKGROUND

Infectious diseases have been one of main diseases faced by human beings. In our country, the treatment of infectious diseases has always been an important and thorny issue. The situation of drug resistant bacteria is especially higher than that of developed countries. Demand for all kinds of drug resistant bacteria is also higher than that of developed countries. As matter of fact, the situation of drug resistant bacteria will still emerge gradually, even if uses of antibiotics are well controlled clinically. Therefore, the struggle between human being and bacterial infections is long and lasting. Under the background of developed countries having slashed spending on research and development to combat drug-resistant bacteria at the end of the last century, fatal incidents caused by "super bacteria" have renewed public concerns about bacterial infections. Glycopeptide compounds have high inhibitory activity against bacteria including methicillin-resistant *Staphylococcus aureus* (MRSA), and their representative drug is vancomycin. However, with clinical application, vancomycin-resistant enterococci (VRE) and MRSA bacteria with reduced activity to vancomycin appeared. By modifying the structure of existing glycopeptide compounds, a series of new structural compounds may be obtained. These new compounds can resist drug-resistant bacteria and have potential advantages in safety and other aspects. Many vancomycin compounds and other glycopeptide compounds are known in the art. Please refer to patents such as U.S. Pat. Nos. 6,635,618B2, 6,392,012B1, 5,840,684, 8,420,592B2, WO0039156A1, WO0183521A2, WO2011019839A2, EP0435503A1, etc., and references such as Bioorg Med Chem Lett, 2003, 13(23):4165-4168, Curr Med Chem, 2001, 8(14):1759-1773 and Expert Opin Invest Drugs, 2007, 16(3):347-357 etc. regarding reports of glycopeptide compounds.

In the existing reports, the Chinese invention patent publication No. CN101928331A discloses a novel glycopeptide compound represented by general formula II of the present invention, and its structure is characterized in that having Vancomylamine on amino acid residues at positions 4- and 6- of the peptide skeleton. Compounds of general formula II have a new structure compared to conventional glycopeptides and have higher antibacterial activity than vancomycin. The research of the present invention is to continue to optimize this modification of the structure on the basis of the existing research in order to obtain new compounds with outstanding characteristics.

SUMMARY OF THE INVENTION

The inventors of the present invention chemically modified structures of glycopeptide antibiotic compounds and obtained improved glycopeptide antibiotic compounds by using compounds of the Chinese patent publication No. CN101928331A as raw materials. Upon testing, compared with a second-generation glycopeptide drug oritavancin, the glycopeptide antibiotic compounds of the present invention have higher inhibition activity on drug-resistant bacterial strains, especially MRSA or VRE. Further testing shows that most of the glycopeptide compounds have safety higher than that of oritavancin and can be prepared into drugs for treating or preventing diseases caused by various bacterial infections, such as skin and soft tissue infections, meningitis, sepsis, pneumonia, arthritis, peritonitis, bronchitis, and empyema.

The first purpose of the present invention is to provide glycopeptide compounds having activity of resisting drug-resistant bacteria, and conforms to the glycopeptide compounds shown in general formula I:

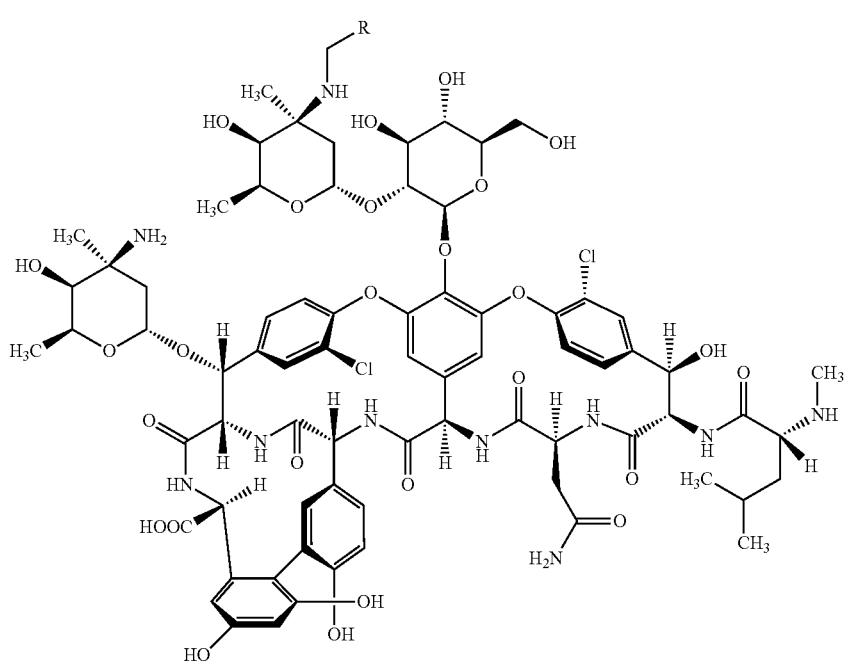

I or a pharmaceutically acceptable salt thereof, wherein:
R represents by the following formula: -A-D-E-G; wherein:
A is a benzene ring;
D is —O—, or —S—, or —NH—;
E is —(CH$_2$)m-, wherein m is 1 to 3;
G is a structural formula:

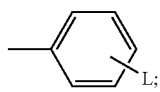

wherein L is any one of hydrogen, methyl, halogen, trifluoromethyl, and methoxy.

According to a preferred embodiment of the present invention, R comprises 4-phenylmethoxyphenyl, 4-phenylethoxyphenyl, 4-phenylpropoxyphenyl, 4-(4'-methylphenylmethoxy)phenyl, 4-(4'-chlorophenylmethoxy)phenyl, 4-(4'-methylphenylethoxy)phenyl, 4-(4'-fluorophenylethoxy)phenyl, 4-(4'-chlorophenylethoxy)phenyl, 4-(4'-bromophenylethoxy)phenyl, 4-(3'-bromophenylethoxy)) phenyl, 4-(4'-trifluoromethylphenylethoxy)phenyl, 4-(4'-methoxyphenylethoxy)phenyl, 4-(4'-chlorophenylpropoxy)) phenyl, 4-benzylthio; phenyl, 4-(4'-chlorobenzylthio) phenyl, 4-(4'-chlorophenylethylthio)phenyl, 4-benzylaminophenyl, 4-(4'-methylbenzylamino)phenyl, 4-(4'-chlorobenzylamino)phenyl, 4-phenylethylaminophenyl, 4-(4'-chlorophenylethylamino) phenyl, 4-(4'-trifluoromethylphenylethylamino)phenyl, 4-(4'-methoxyphenylethylamino)phenyl, 4-amphetamine phenyl and 4-(4'-chloramphetamine)phenyl.

The second purpose of the present invention is to provide a pharmaceutical preparation comprising the glycopeptide compounds having activity of resisting drug-resistant bacteria as an active ingredient as described above. The pharmaceutical preparation may be injections, oral preparations, transfusions or external preparations. It can be administered to patients in need of treatment by intravenous injection, subcutaneous injection or oral administration. It can be prepared into solid preparations, such as tablets, powders or capsules when being used for oral administration. It can be prepared into injections for injection. It can be made into ointment, powder or loaded on a carrier when being used for external use. Various dosage forms of the pharmaceutical preparations of the present invention can be prepared by conventional methods in the medical field, wherein the weight percentage of glycopeptide compounds as the active ingredient is 0.1%-99.9%, and preferably, the weight percentage is 0.5%-90%.

A general dosage of the above-mentioned pharmaceutical preparations applied to patients in need of treatment may refer to existing dosages of vancomycin, norvancomycin and oritavancin. For example, it may be 0.1-2.0 g/d for adults. specific dosages can be based on the patient's age and disease changes The glycopeptide compounds of the present invention can be prepared into salts by conventional methods, for example, prepared into hydrochloride.

The third purpose of the present invention is to provide a method of preparing for the aforementioned glycopeptide compounds having activity of resisting drug-resistant bacteria.

The following description is a representative method for preparing for the glycopeptide compounds having activity of resisting drug-resistant bacteria of the present invention. The preparation of the glycopeptide compounds is not intended to be limited to the type of method. Of course, it can be carried out by other methods. It will be possible to understand that other process conditions can also be used although typical or preferred process conditions (such as reaction solvent, reaction temperature, molar ratio of feed materials, etc.) are given, unless otherwise specified. Optimum process conditions may vary depending on specific reactants or solvents used. But those skilled in the art can easily determine such conditions with the aid of conventional process conditions.

In addition, it will be obvious to those skilled in the art that conventional protecting groups may be necessary or need in order to prevent certain functional groups from undergoing unwanted reactions. Selection of suitable protecting groups for specific functional groups and suitable conditions for protection and deprotection of such functional groups are well known in the art. If desired, those protective groups other than those described herein may be used. For example, various protective groups and their introduction or removal are described in T. W. Greene and G. M. Wuts, Protective Groups in Organic Synthesis, 3rd, Wiley, New York, 1999 and references cited therein.

In the present invention, the compound of general formula I can be prepared by the following synthetic route:

(1) when D is —O— or —S—, in particular, R is 4-phenylmethoxyphenyl, 4-phenylethoxyphenyl, 4-phenylpropoxyphenyl, 4-(4'-methylphenylmethoxy)phenyl, 4-(4'-chlorophenylmethoxy)phenyl, 4-(4'-methylphenylethoxy)phenyl, 4-(4'-fluorophenylethoxy)phenyl, 4-(4'-chlorophenylethoxy)phenyl, 4-(4'-bromophenylethoxy)phenyl, 4-(3'-bromophenylethoxy))phenyl, 4-(4'-trifluoromethylphenylethoxy)phenyl, 4-(4'-methoxyphenylethoxy)phenyl, 4-(4'-chlorophenylpropoxy))phenyl, 4-benzylthio; phenyl, 4-(4'-chlorobenzylthio)phenyl, 4-(4'-chlorophenylethylthio)phenyl, the compound shown in the structural formula II reacts with aldehyde and borane tert-butylamine to obtain the compound of general formula I:

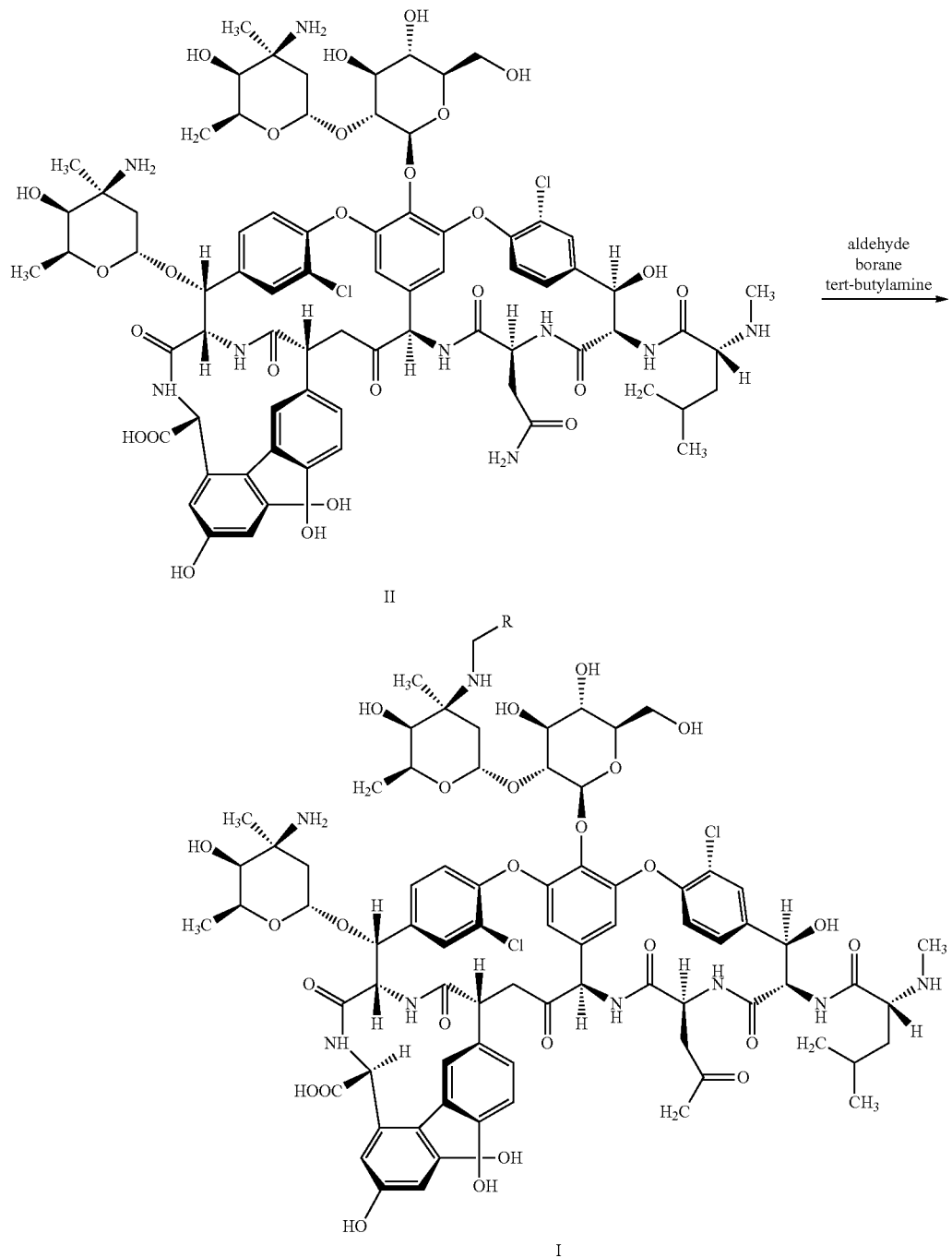

(2) when D is —NH—, in particular, R is 4-benzylaminophenyl, 4-(4'-methylbenzylamino)phenyl, 4-(4'-chlorobenzylamino)phenyl, 4-phenyl ethylaminophenyl, 4-(4'-chlorophenylethylamino) phenyl, 4-(4'-trifluoromethylphenylethylamino)phenyl, 4-(4'-methoxyphenylethylamino)phenyl, 4-amphetamine phenyl and 4-(4'-chloramphetamine)phenyl, the compound shown in general formula II reacts with aldehyde and borane tert-butylamine and diethylamine to obtain the compound of general formula I:

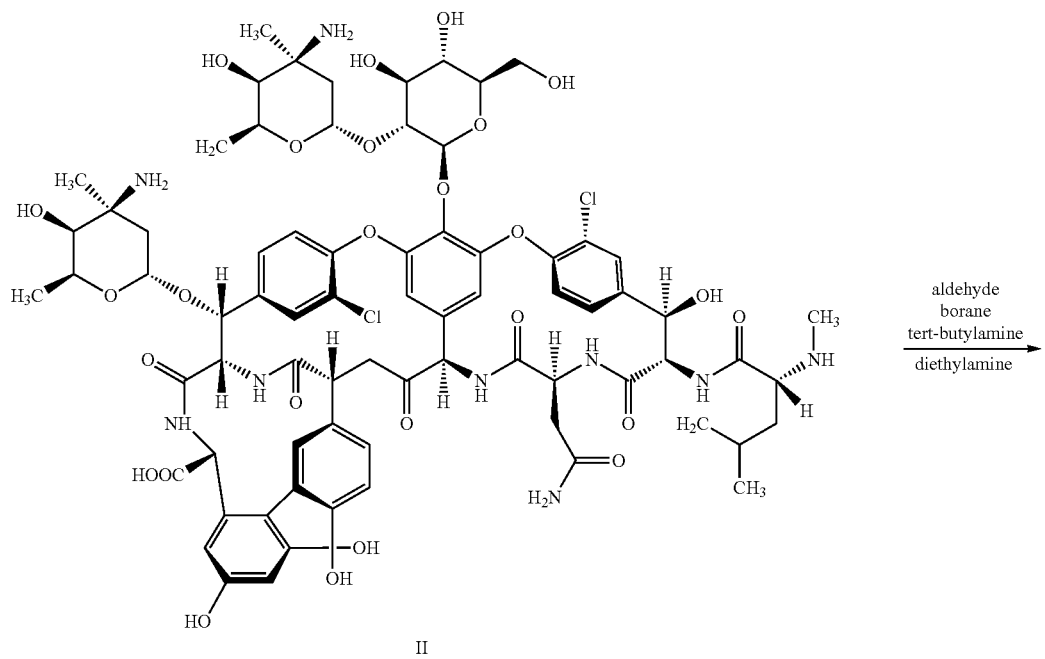

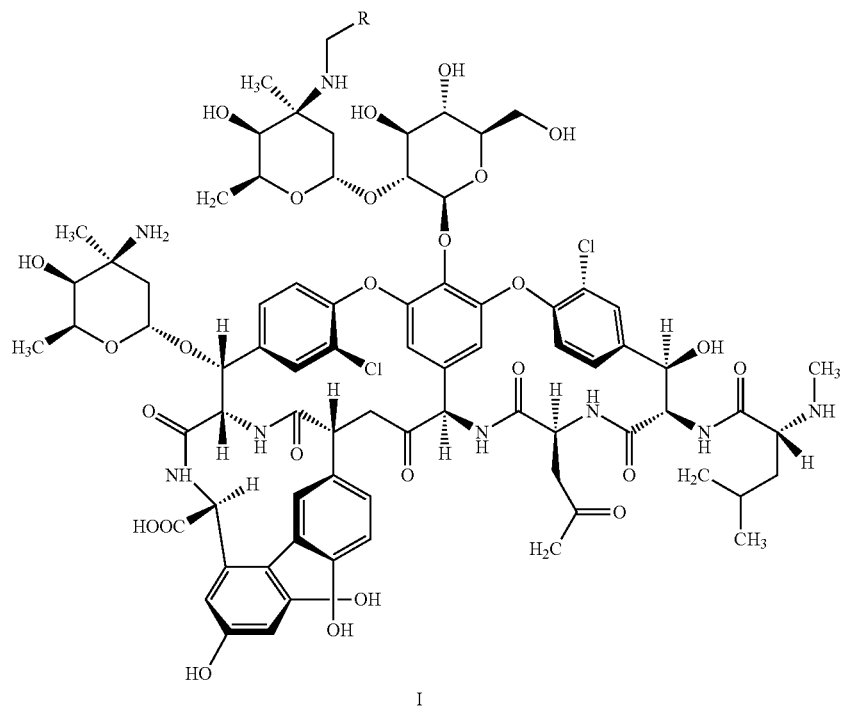

Usually, the above reaction is carried out in this way as follows: using one or several organic solvents (such as DMF, DMSO, methanol, ethanol, etc.), preferably using a mixed solvent of DMF and methanol, in excess of amine (usually about 2 equivalents), such as in the presence of DIEA, at a temperature of about 0° C.-100° C., preferably a temperature of 65° C., the compound of general formula II mixs with about 0.5-2.5 equivalents, preferably 1.3 equivalents of aldehyde for 0.5-4 hours to obtain a reactant, and then cool the reactant to about 0° C.-40° C., preferably cool the reactant to room temperature; add excess acid (usually about 3 equivalents) to the reactant, such as trifluoroacetic acid, and afterwards add a commonly defined reducing agent (such as sodium borohydride, sodium cyanoborohydride, sodium triacetoxyborohydride, borane tert-butylamine, borane pyridine, etc.), preferably borane tert-butylamine (usually about 2 equivalents); and then mix together at about 0° C.-100° C., preferably at room temperature, until the reaction is substantially completed. After the reaction is completed, carrying out conventional separation and purification processes such as silica gel, ion exchange resins, polymer fillers, C18 liquid phase prepared, solvent precipitation, crystallization, etc., preferably carrying out separation and purification by polymer fillers, in order to obtain the compound of general formula I.

After the above reaction is completed, any protective groups present in the product are removed by using well-known methods and generally applicable reagents, such as organic acids, inorganic acids, organic bases, inorganic bases, catalytic hydrogenation, alkaline hydrolysis, etc.; preferably organic base, for example, remove the Fmoc protecting group in the product by using diethylamine. After the reaction is completed, conventional separation and purification processes are used for obtaining the compound of general formula I, such as silica gel, ion exchange resins, polymer fillers, C18 liquid phase prepared, solvent precipitation, crystallization, etc., preferably polymer fillers are used for separation and purification.

Aldehydes, reaction reagents and purification devices suitable for the above-mentioned reaction route are all commercially available.

According to a preferred embodiment of the present invention, the aldehyde is selected from any one of 4-phenylmethoxybenzaldehyde, 4-phenylethoxybenzaldehyde, 4-phenylpropoxybenzaldehyde, 4-(4'-methylphenylmethoxy)benzaldehyde, 4-(4'-chlorophenylmethoxy)benzaldehyde, 4-(4'-methylphenylethoxy)benzaldehyde, 4-(4'-fluorophenylethoxy)benzaldehyde, 4-(4'-chlorophenylethoxy)benzaldehyde, 4-(4'-bromophenylethoxy)benzaldehyde, 4-(3'-bromophenylethyoxy)benzaldehyde, 4-(4'-trifluoromethylphenylethoxy)benzaldehyde, 4-(4'-methoxyphenylethoxy)benzaldehyde, 4-(4'-chlorophenylpropoxy)benzaldehyde, 4-benzylthiobenzaldehyde, 4-(4'-chlorobenzylthio)benzaldehyde, 4-(4'-chlorophenylethylthio)benzaldehyde, 4-(N-Fmoc-benzylamino)benzaldehyde, 4-(4'-methyl-N-Fmoc-benzylamino)benzaldehyde, 4-(4'-chloro-N-Fmoc-benzylamino)benzaldehyde, 4-(N-Fmoc-phenylethylamino) benzaldehyde, 4-(4'-chloro-N-Fmoc-phenylethylamino) benzaldehyde, 4-(4'-trifluoromethyl-N-Fmoc-phenylethylamino)benzaldehyde, 4-(4'-methoxy-N-Fmoc-phenylethylamino)benzaldehyde, 4-(N-Fmoc-amphetamino)benzaldehyde and 4-(4'-chloro-N-Fmoc-amphetamino)benzaldehyde.

The fourth purpose of the present invention is to provide an application of the glycopeptide compounds as described above in the preparation of drugs for the treatment of drug-resistant bacterial infectious diseases.

According to a preferred embodiment of the present invention, the drug-resistant bacteria are Gram-positive drug-resistant bacteria.

According to a preferred embodiment of the present invention, the drug-resistant bacteria are methicillin-resistant *Staphylococcus aureus* or vancomycin-resistant *enterococcus*.

Upon testing, compared with a second-generation glycopeptide drug oritavancin, the glycopeptide antibiotic compounds have higher inhibition activity on drug-resistant bacterial strains, especially MRSA or VRE. Further testing shows that most of the glycopeptide compounds have safety higher than that of oritavancin and can be prepared into drugs for treating or preventing diseases caused by various bacterial infections, such as skin and soft tissue infections, meningitis, sepsis, pneumonia, arthritis, peritonitis, bronchitis, and empyema.

DETAILED DESCRIPTION OF THE INVENTION

The present invention will be further described below in conjunction with specific embodiments. It should be understood that the following examples are only used to illustrate the present invention and not to limit the scope of the present invention.

In the present invention, the following abbreviations have the following meanings. Undefined abbreviations have their generally accepted meanings, unless otherwise stated, all of room temperature are referred to as a temperature of 20° C.-30° C.

DIEA: N,N-diisopropylethylamine
DMF: N,N-dimethylformamide
DMSO: dimethyl sulfoxide
ESI: electrospray ionization mass spectrometry
Fmoc: 9-fluorenyl methoxycarbonyl
H: hour
LD50: median lethal dose
MRSA: Methicillin-resistant *Staphylococcus aureus*
MIC: minimum inhibitory concentration
MS: mass spectrum
TFA: trifluoroacetic acid
VRE: Vancomycin-resistant *Enterococcus*

In the present invention, the method for obtaining the compound of general formula II refers to the patent application document of the Chinese patent publication No. CN101928331A. Other raw materials, materials and devices of the present invention are all commercially available.

In the following examples, reverse-phase polymer fillers Uni PS25-300 and Uni PSA30-300 are used for purifying synthesized crude products. After dissolving crude product into methanol (or acetonitrile) aqueous solution, load the sample onto a glass chromatography column with filler at a flow rate of 1 times column volume/h. After loading sample, pre-wash with methanol (or acetonitrile) aqueous solution for 1 hour, and then elute with methanol (or acetonitrile) aqueous solution containing TFA at a flow rate of 1.5 times column volume/h. After eluting 1 times column volume, start with collecting the eluent, concentrate and dry the eluent in order to obtain pure products of each sample.

In the following examples, the ratio of the eluent is referred to as a volume percentage, and the yield is referred to as a molar yield, unless otherwise specified.

The structure of each compounds of the following examples is shown in Table 1.

TABLE 1

Structures of Each Compounds

| Number | R | Molecular formula | MS (ESI) |
|---|---|---|---|
| 1 | —C₆H₄—O—CH₂—C₆H₅ | C₈₇H₁₀₀Cl₂N₁₀O₂₇ | 1787.60 [M + H]+ |
| 2 | —C₆H₄—O—CH₂—CH₂—C₆H₅ | C₈₈H₁₀₂Cl₂N₁₀O₂₇ | 1801.63 [M + H]+ |
| 3 | —C₆H₄—O—CH₂—CH₂—CH₂—C₆H₅ | C₈₉H₁₀₄Cl₂N₁₀O₂₇ | 1815.64 [M + H]+ |
| 4 | —C₆H₄—O—CH₂—C₆H₄—CH₃ | C₈₈H₁₀₂Cl₂N₁₀O₂₇ | 1801.63 [M + H]+ |
| 5 | —C₆H₄—O—CH₂—C₆H₄—Cl | C₈₇H₉₉Cl₃N₁₀O₂₇ | 1821.56 [M + H]+ |
| 6 | —C₆H₄—O—CH₂—CH₂—C₆H₄—CH₃ | C₈₉H₁₀₄Cl₂N₁₀O₂₇ | 1815.61 [M + H]+ |
| 7 | —C₆H₄—O—CH₂—CH₂—C₆H₄—F | C₈₈H₁₀₁Cl₂FN₁₀O₂₇ | 1819.62 [M + H]+ |
| 8 | —C₆H₄—O—CH₂—CH₂—C₆H₄—Cl | C₈₈H₁₀₁Cl₃N₁₀O₂₇ | 1835.60 [M + H]+ |
| 9 | —C₆H₄—O—CH₂—CH₂—C₆H₄—Br | C₈₈H₁₀₁BrCl₂N₁₀O₂₇ | 1879.54 [M + H]+ |
| 10 | —C₆H₄—O—CH₂—CH₂—C₆H₄—Br (meta) | C₈₈H₁₀₁BrCl₂N₁₀O₂₇ | 1879.54 [M + H]+ |
| 11 | —C₆H₄—O—CH₂—CH₂—C₆H₄—CF₃ | C₈₉H₁₀₁Cl₂F₃N₁₀O₂₇ | 1869.64 [M + H]+ |
| 12 | —C₆H₄—O—CH₂—CH₂—C₆H₄—OCH₃ | C₈₉H₁₀₄Cl₂N₁₀O₂₈ | 1831.64 [M + H]+ |
| 13 | —C₆H₄—O—CH₂—CH₂—CH₂—C₆H₄—Cl | C₈₉H₁₀₃Cl₃N₁₀O₂₇ | 1849.62 [M + H]+ |
| 14 | —C₆H₄—S—CH₂—C₆H₅ | C₈₇H₁₀₀Cl₂N₁₀O₂₆S | 1803.59 [M + H]+ |
| 15 | —C₆H₄—S—CH₂—C₆H₄—Cl | C₈₇H₉₉Cl₃N₁₀O₂₆S | 1837.56 [M + H]+ |

TABLE 1-continued

Structures of Each Compounds

| Number | R | Molecular formula | MS (ESI) |
|---|---|---|---|
| 16 | —C6H4—S—CH2—CH2—C6H4—Cl | $C_{88}H_{101}Cl_3N_{10}O_{26}S$ | 1851.57 [M + H]+ |
| 17 | —C6H4—NH—CH2—C6H5 | $C_{87}H_{101}Cl_2N_{11}O_{26}$ | 1786.64 [M + H]+ |
| 18 | —C6H4—NH—CH2—C6H4—CH3 | $C_{88}H_{103}Cl_2N_{11}O_{26}$ | 1800.65 [M + H]+ |
| 19 | —C6H4—NH—CH2—C6H4—Cl | $C_{87}H_{100}Cl_3N_{11}O_{26}$ | 1820.57 [M + H]+ |
| 20 | —C6H4—NH—CH2—CH2—C6H5 | $C_{88}H_{103}Cl_2N_{11}O_{26}$ | 1800.65 [M + H]+ |
| 21 | —C6H4—NH—CH2—CH2—C6H4—Cl | $C_{88}H_{102}Cl_3N_{11}O_{26}$ | 1834.60 [M + H]+ |
| 22 | —C6H4—NH—CH2—CH2—C6H4—CF3 | $C_{89}H_{102}Cl_2F_3N_{11}O_{26}$ | 1868.63 [M + H]+ |
| 23 | —C6H4—NH—CH2—CH2—C6H4—OCH3 | $C_{89}H_{105}Cl_2N_{11}O_{27}$ | 1830.65 [M + H]+ |
| 24 | —C6H4—NH—CH2—CH2—CH2—C6H5 | $C_{89}H_{105}Cl_2N_{11}O_{26}$ | 1814.66 [M + H]+ |
| 25 | —C6H4—NH—CH2—CH2—CH2—C6H4—Cl | $C_{89}H_{104}Cl_3N_{11}O_{26}$ | 1848.63 [M + H]+ |

Example 1. Preparation of Compound 1

Mix compound of general formula II (0.5 g, 0.3 mmol) with 10 mL DMF-methanol (1:1, v/v), add DIEA (0.1 mL, 0.6 mmol) and 4-phenylmethoxybenzaldehyde (0.085 g, 0.4 mmol)), stir at 65° C. for 2h and then cool to room temperature; add TFA (0.07 mL, 0.9 mmol) and borane tert-butylamine (0.05 g, 0.6 mmol) and continue to stir at room temperature for 2h to form a reaction solution, and then add methyl tert-butyl ether (50 mL) to the reaction solution, collect a precipitate by suction filtration, purify a residue with reverse-phase polymer filler, elute with methanol-0.04% TFA aqueous solution (1:4, v/v), to obtain Compound 1 (white solid 0.28 g, yield 52%) after concentrating and drying.

The calculated molecular weight of $C_{87}H_{100}Cl_2N_{10}O_{27}$: 1786.61, the measured value: m/z=1787.60 [M+H]+.

Example 2. Preparation of Compound 2

Mix compound of general formula II (0.5 g, 0.3 mmol) with 10 mL DMF-methanol (1:1, v/v), add DIEA (0.1 mL, 0.6 mmol) and 4-phenylethoxybenzaldehyde (0.09 g, 0.4 mmol), stir at 65° C. for 2h and then cool to room temperature; add TFA (0.07 mL, 0.9 mmol) and borane tert-butylamine (0.05 g, 0.6 mmol) and continue to stir at room temperature for 2h to form a reaction solution, and then add methyl tert-butyl ether (50 mL) to the reaction solution, collect a precipitate by suction filtration, purify a residue with reversed-phase polymer filler, elute with methanol-0.04% TFA aqueous solution (1:4, v/v), to obtain concentrated and dried to obtain compound 2 (white solid 0.31 g), yield 57%) after concentrating and drying.

The calculated molecular weight of $C_{88}H_{102}Cl_2N_{10}O_{27}$: 1800.63, the measured value: m/z=1801.63 [M+H]+.

Example 3. Preparation of Compound 3

Mix compound II (1.0 g, 0.6 mmol) with 15 mL DMF-methanol (1:1, v/v), add DIEA (0.2 mL, 1.2 mmol) and 4-phenylpropoxybenzaldehyde (0.2 g, 0.8 mmol), stir at 65° C. for 2h and then cooled to room temperature; add TFA (0.14 mL, 1.8 mmol) and borane tert-butylamine (0.1 g, 1.2 mmol) and continue to stir at room temperature for 2h to form a reaction solution, then add methyl tert-butyl ether (70 mL) to the reaction solution, collect a precipitate by suction filtration, purify a residue with reverse-phase polymer filler, elute with methanol-0.04% TFA aqueous solution (1:4, v/v), to obtain Compound 3 (white solid 0.65 g, yield 60%) after concentrating and drying.

The calculated molecular weight of $C_{89}H_{104}Cl_2N_{10}O_{27}$: 1814.64, the measured value: m/z=1815.64 [M+H]+.

Example 4. Preparation of Compound 4

The preparation method of Compound 4 is the same as that of Compound 1, and the aldehyde used is replaced by 4-(4'-methylphenylmethoxy)benzaldehyde. Compound 4 (white solid 0.3 g, yield 56%) is obtained.

The calculated molecular weight of $C_{68}H_{102}Cl_2N_{10}O_{27}$: 1800.63, the measured value: m/z=1801.63 [M+H]+.

Example 5. Preparation of Compound 8

Mix compound II (1.0 g, 0.6 mmol) with 15 mL DMF-methanol (1:1, v/v), add DMA (0.2 mL, 1.2 mmol) and 4-(4'-chlorophenylethoxy) benzaldehyde (0.21 g, 0.8 mmol), stir at 65° C. for 2 h, then cooled to room temperature; and then add TFA (0.14 mL, 1.8 mmol) and borane tert-butylamine (0.1 g, 1.2 mmol) and continue to stir at room temperature for 2h to form a reaction solution, then add methyl tert-butyl ether (70 mL) to the reaction solution, collect a precipitate by suction filtration, purify a residue with reverse-phase polymer filler, elute with methanol-0.04% TFA aqueous solution (1:4, v/v), to obtain Compound 8 (white solid 0.55 g, yield 50%) after concentrating and drying.

The calculated molecular weight of $C_{88}H_{101}Cl_3N_{10}O_{27}$: 1834.59, the measured value: m/z=1835.60 [M+H]+.

Example 6. Preparation of Compound 10

Mix Compound II (1.0 g, 0.6 mmol) with 15 mL DMF-methanol (1:1, v/v), add DIEA (0.2 mL, 1.2 mmol) and 4-(3'-bromophenylethoxy)benzaldehyde (0.24 g, 0.8 mmol), stir at 65° C. for 2h and then cool to room temperature; and then add TFA (0.14 mL, 1.8 mmol) and borane tert-butylamine (0.1 g, 1.2 mmol) and stir at room temperature for 2h to form a reaction solution, then add methyl tert-butyl ether (70 mL) to the reaction solution, collect a precipitate by suction filtration, purify a residue with reverse-phase polymer filler, elute with methanol-0.04% TFA aqueous solution (1:4, v/v), to obtain Compound 10 (white solid 0.65 g, yield 58%) after concentrating and drying.

The calculated molecular weight of $C_{88}H_{101}BrCl_2N_{10}O_{27}$: 1878.54, the measured value: m/z=1879.54 [M+H]+.

Example 7. Preparation of Compound 11

The preparation method of Compound 11 is the same as that of Compound 8, and the aldehyde used is replaced by 4-(4'-trifluoromethylphenylethoxy)benzaldehyde. Compound 11 (white solid 0.68 g, yield 61%) is obtained.

The calculated molecular weight of $C_{89}H_{101}Cl_2F_3N_{10}O_{27}$: 1868.62, the measured value: m/z=1869.64 [M+H]+.

Example 8. Preparation of Compound 12

Mix compound II (0.5 g, 0.3 mmol) with 10 mL DMF-methanol (1:1, v/v), add DIEA (0.1 mL, 0.6 mmol) and 4-(4'-methoxyphenylethoxy)benzaldehyde (0.1 g, 0.4 mmol), stir at 65° C. for 2h and then cool to room temperature; and then add TFA (0.07 mL, 0.9 mmol) and borane tert-butylamine (0.05 g, 0.6 mmol) and continue to stir at room temperature for 2h to form a reaction solution, and then add tert-butyl ether (50 mL) to the reaction solution, and collect a precipitate by suction filtration, purify a residue with reversed-phase polymer filler, elute with methanol-0.04% TFA aqueous solution (1:4, v/v), to obtain Compound 12 (white solid 0.22 g, yield 40%) after concentrating and drying.

The calculated molecular weight of $C_{89}H_{104}Cl_2N_{10}O_{28}$: 1830.64, the measured value: m/z=1831.64 [M+H]+.

Example 9. Preparation of Compound 13

The preparation method of Compound 13 is the same as that of Compound 12, and the aldehyde used is replaced by 4-(4'-chlorophenylpropoxy)benzaldehyde, to obtain Compound 13 (white solid 0.31 g, yield 56%).

The calculated molecular weight of $C_{89}H_{103}Cl_3N_{10}O_{27}$ 1848.61, the measured value: m/z=1849.62 [M+H]+.

Example 10. Preparation of Compound 16

Mix compound II (1.0 g, 0.6 mmol) with 15 mL DMF-methanol (1:1, v/v), add DIEA (0.2 mL, 1.2 mmol) and 4-(4'-chlorophenylethylthio) benzaldehyde (0.22 g, 0.8 mmol), stir at 65° C. for 2h and then cool to room temperature; and then add TFA (0.14 mL, 1.8 mmol) and borane tert-butylamine (0.1 g, 1.2 mmol) and continue to stir at room temperature for 2h to form a reaction solution, and then add methyl tert-butyl ether (70 mL) to the reaction solution, collect a precipitate by suction filtration, purify a residue with reverse-phase polymer filler, elute with methanol-0.04% TFA aqueous solution (1:4, v/v), to obtain compound 16 (white solid 0.55 g, yield 50%) after concentrating and drying.

The calculated molecular weight of $C_{88}H_{101}Cl_3N_{10}O_{26}S$: 1850.57, the measured value: m/z=1851.57 [M+H]+.

Example 11. Preparation of Compound 18

Stir Compound II (0.5 g, 0.3 mmol) with 10 mL DMF-methanol (1:1, v/v), add DIEA (0.1 mL, 0.6 mmol) and 4-(4'-methyl-N-Fmoc-benzylamino) benzaldehyde (0.18 g, 0.4 mmol), stir at 65° C. for 2h and then cool to room temperature, and then add TFA (0.07 mL, 0.9 mmol) and borane tert-butylamine (0.05 g, 0.6 mmol) and continue to stir at room temperature for 2h; and then add diethylamine (1 mL) for 3h under stirring again to form a reaction solution, add methyl tert-butyl ether (50 mL) to the reaction solution, collect a precipitate by suction filtration, and purify a residue with reverse-phase polymer filler, elute with methanol-0.04% TFA aqueous solution (1:4, v/v), to obtain Compound 18 (white solid 0.24 g, yield 44%) after concentrating and drying.

The calculated molecular weight of $C_{88}H_{103}Cl_2N_{11}O_{26}$: 1799.65, the measured value: m/z=1800.65 [M+H]+.

Example 12. Preparation of Compound 20

The preparation method of Compound 20 is the same as that of Compound 18, and the aldehyde used is replaced by 4-(N-Fmoc-phenylethylamino)benzaldehyde. Compound 20 (white solid 0.35 g, yield 65%) is obtained.

The calculated molecular weight of $C_{88}H_{103}Cl_2N_{11}O_{26}$: 1799.65, the measured value: m/z=1800.65 [M+H]+.

Example 13. Preparation of Compound 21

Mix compound II (0.5 g, 0.3 mmol) with 10 mL DMF-methanol (1:1, v/v), add DIEA (0.1 mL, 0.6 mmol) and 4-(4'-chloro-N-Fmoc-phenylethylamino)benzaldehyde (0.19 g, 0.4 mmol), stir at 65° C. for 2h and then cool to room temperature, and then add TFA (0.07 mL, 0.9 mmol) and borane tert-butylamine (0.05 g, 0.6 mmol) and stir at room temperature for 2h, and then add diethylamine (1 mL) for 3h under stirring again to form a reaction solution, add methyl tert-butyl ether (50 mL) to the reaction solution, and then collect a precipitate by suction filtration; purify the residue with a reversed-phase polymer filler, elute with methanol-0.04% TFA aqueous solution (1:4, v/v), to obtain compound 21 (white solid 0.2 g, yield 36%) after concentrating and drying.

The calculated molecular weight of $C_{88}H_{102}Cl_3N_{11}O_{26}$: 1833.61, the measured value: m/z=1834.60 [M+H]+.

Example 14. Preparation of Compound 23

The preparation method of Compound 23 is the same as that of Compound 21, and the aldehyde used is replaced by 4-(4'-methoxy-N-Fmoc-phenylethylamino)benzaldehyde. Compound 23 (white solid 0.3 g, yield 55%) is obtained.

The calculated molecular weight of $C_{89}H_{105}Cl_2N_{11}O_{27}$: 1829.66, the measured value: m/z=1830.65 [M+H]+.

Example 15. Preparation of Compound 25

Mix compound of general formula II (0.5 g, 0.3 mmol) with 10 mL DMF-methanol (1:1, v/v), add DMA (0.1 mL, 0.6 mmol) and 4-(4'-chloro-N-Fmoc-amphetamine)benzaldehyde (0.2 g, 0.4 mmol), stir at 65° C. for 2h and then cool to room temperature, and then add TFA (0.07 mL, 0.9 mmol) and borane tert-butylamine (0.05 g, 0.6 mmol) and continue to stir at room temperature for 2h, and then add diethylamine (1 mL) and stir for 3h again to form a reaction solution, add methyl tert-butyl ether (50 mL) to the reaction solution, and then collect a precipitate by suction filtration; purify a residue with reversed-phase polymer filler, elute with methanol-0.04% TFA aqueous solution (1:4. V/v), to obtain compound 25 (white solid 0.36 g, yield 65%) after concentrating and drying.

The calculated molecular weight of $C_{89}H_{104}Cl_3N_{11}O_{26}$: 1847.62, the measured value: m/z=1848.63 [M+H]+.

Example 16. Example of Salt Formation

Add 50 mg of Compound 8 to 1 mL of saturated hydrogen chloride methanol solution, stir at room temperature, and lyophilize it in order to obtain a white solid 50 mg of hydrochloride salt of Compound 8.

In addition, respectively use hydrobromic acid, sulfuric acid, nitric acid, phosphoric acid, formic acid, acetic acid, propionic acid, oxalic acid, malonic acid, succinic acid, fumaric acid, maleic acid, lactic acid, malic acid, tartaric acid, citric acid, picric acid, methanesulfonic acid, aspartic acid or glutamic acid instead of hydrogen chloride in the above-mentioned saturated hydrogen chloride methanol solution, in order to obtain a corresponding salt.

Example 17. Examples of Preparation

It should be noted that the Example is only for illustration and is not intended to limit the scope of the present invention. The term "active ingredient" is referred to as compounds, solvates, tautomers, optical isomers, prodrugs, pharmaceutically acceptable salts, etc. of the present invention.

A intravenous preparation can be prepared as follows:
Active ingredient: 100 mg
Isotonic saline: 1000 mL Solutions of the above components are intravenously administered to patients at a rate of 1 mL/min usually.

Example 18. Determination of the Antibacterial Activity of the Compound

An antibacterial activity of the compounds in Table 1 is determined in vitro, and a minimum inhibitory concentration (MIC) is read. The determination method refers to the method of the Pharmacopoeia of the People's Republic of China (2015 edition). The MRSA detection strain is purchased from ATCC, and the VRE detection strain is from the clinically isolated drug-resistant strain 07-W3-45 from Shanghai Huashan Hospital. Known antibiotic oritavancin (phosphate) is used for a reference drug. The comparison test results are shown in the Table 2.

A zebrafish toxicity test of the compounds in Table 1 is also tested. Randomly select wild AB zebrafish in a six-well plate, and inject each test sample at a dose of 50, 100, 150, 200, and 250 ng/tail intravenously. At the same time, a normal control group and a solvent control group (aqueous phosphoric acid) are set; During this experiment, the death of zebrafish is observed and recorded every day and the dead fish are removed. After 72 hours of treatment, the death of zebrafish is counted. Calculate the LD50 of each test product to zebrafish. The results are combined in Table 2.

TABLE 2

MIC (μg/mL) zebrafish LD50 of each compound in Table 1 to MRSA and VRE

| | MIC (μg/mL) | | |
| --- | --- | --- | --- |
| Compound | ATCC43300 (MRSA) | Clinical isolates 07-W3-45 (VRE) | Zebrafish$LD_{50}$ (ng/tail) |
| Orivancin | 0.5 | 2 | 89.4 |
| 1 | 0.5 | 2 | 139 |
| 2 | 0.5 | 2 | 163 |
| 3 | 0.25 | 1 | 123 |
| 4 | 0.5 | 2 | 101 |
| 5 | 0.5 | 2 | 180 |
| 6 | 0.25 | 8 | 121 |
| 7 | 0.5 | 1 | 97 |
| 8 | 0.5 | 1 | 150 |
| 9 | 0.25 | 1 | 129 |
| 10 | 0.125 | 1 | 113 |
| 11 | 0.064 | 0.5 | 99 |
| 12 | 0.5 | 16 | 188 |
| 13 | 0.5 | 2 | 164 |
| 14 | 0.032 | 8 | 82 |
| 15 | 0.032 | 1 | 76 |
| 16 | 0.032 | 0.5 | 72 |
| 17 | 0.5 | 1 | 139 |
| 18 | 0.5 | 1 | 128 |
| 19 | 0.25 | 0.2 | 117 |
| 20 | 0.5 | 2 | 189 |
| 21 | 0.016 | 0.5 | 102 |
| 22 | 0.032 | 0.25 | 142 |
| 23 | 0.5 | 1 | 192 |
| 24 | 0.5 | 1 | 153 |
| 25 | 0.064 | 0.25 | 97 |

All samples are tested for zebrafish toxicity in phosphate form.

It can be seen from Table 2 that the glycopeptide compounds of the present invention have higher inhibitory activity or less toxicity against drug-resistant strains MRSA or VRE, and is higher security, compared to the second-generation glycopeptide drug oritavancin.

The present invention is illustrated by the above examples, however, should understand that the present invention is not limited to special instance and implementation scheme described above. For those skilled in the art, any equivalent modifications and substitutions made to the invention are also within the scope of the invention. Therefore, all equivalent changes and modifications made without departing from the spirit and scope of the present invention should be covered within the scope of the present invention.

We claim:

1. A glycopeptide compound having activity of resisting drug-resistant bacteria of methicillin-resistant *Staphylococcus aureus* (MRSA) and vancomycin-resistant enterococci (VRE), characterized in that, conforming glycopeptide compounds shown in general formula I:

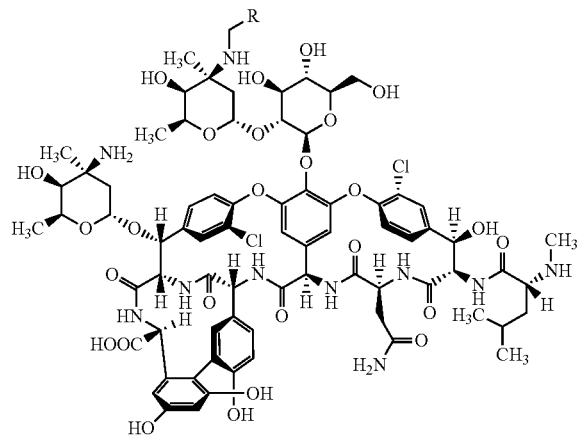

I or a pharmaceutically acceptable salt thereof, wherein:

R represents by the following formula: -A-D-E-G; wherein:

A is a benzene ring;

D is —O— or —NH—;

E is —(CH$_2$)m-, wherein m is 1 to 3;

G is the structural formula:

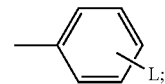

wherein L is any one of halogen, trifluoromethyl, and methoxy.

2. The glycopeptide compounds according to claim 1, wherein R is selected from:

4-(4'-chlorophenylmethoxy)phenyl,
4-(4'-fluorophenylethoxy)phenyl,
4-(4'-chlorophenylethoxy)phenyl,
4-(4'-bromophenylethoxy)phenyl,
4-(3'-bromophenylethoxy)phenyl,
4-(4'-trifluoromethylphenylethoxy)phenyl,
4-(4'-methoxyphenylethoxy)phenyl,
4-(4'-chlorophenylpropoxy)phenyl,
4-(4'-chlorobenzylamino)phenyl,
4-(4'-chlorophenylethylamino)phenyl,
4-(4'-trifluoromethylphenylethylamino)phenyl, and
4-(4'-chloramphetamine)phenyl.

* * * * *